(12) United States Patent
Hertz et al.

(10) Patent No.: US 10,085,702 B2
(45) Date of Patent: Oct. 2, 2018

(54) X-RAY MICRO IMAGING

(71) Applicant: JETTEC AB, Stocksund (SE)

(72) Inventors: Hans Martin Hertz, Stocksund (SE);
Jakob Christer Larsson, Stockholm (SE); Ulf Lundström, Solna (SE);
Hans Daniel Larsson, Stockholm (SE);
Carmen Mihaela Vogt, Järfälla (SE)

(73) Assignee: JETTEC AB, Stocksund (SE)

( * ) Notice: Subject to any disclaimer, the term of this patent is extended or adjusted under 35 U.S.C. 154(b) by 200 days.

(21) Appl. No.: 15/110,355

(22) PCT Filed: Jan. 2, 2015

(86) PCT No.: PCT/EP2015/050011
§ 371 (c)(1),
(2) Date: Jul. 7, 2016

(87) PCT Pub. No.: WO2015/104225
PCT Pub. Date: Jul. 16, 2015

(65) Prior Publication Data
US 2016/0331336 A1 Nov. 17, 2016

(30) Foreign Application Priority Data
Jan. 7, 2014 (SE) ...................................... 1450003

(51) Int. Cl.
*A61B 6/00* (2006.01)
*A61B 6/03* (2006.01)
(Continued)

(52) U.S. Cl.
CPC .............. *A61B 6/485* (2013.01); *A61B 6/032* (2013.01); *A61B 6/037* (2013.01); *A61B 6/40* (2013.01);
(Continued)

(58) Field of Classification Search
CPC .................................................... A61B 6/4035
See application file for complete search history.

(56) References Cited

U.S. PATENT DOCUMENTS

2012/0265050 A1* 10/2012 Wang ..................... A61B 5/055
600/411

FOREIGN PATENT DOCUMENTS

| EP | 1 305 984 B1 | 11/2010 |
|----|---|---|
| EP | 2 741 309 A1 | 6/2014 |
| WO | WO 2011/084625 A1 | 7/2011 |

OTHER PUBLICATIONS

International Search Report (PCT/ISA/210) dated Mar. 18, 2015, by the European Patent Office as the International Searching Authority for International Application No. PCT/EP2015/050011.
(Continued)

*Primary Examiner* — Dani Fox
(74) *Attorney, Agent, or Firm* — Buchanan Ingersoll & Rooney P.C.

(57) ABSTRACT

The disclosure provides improvements of resolution and contrast in the field of x-ray imaging by using a line emitting, quasi-monochromatic x-ray source for x-ray fluorescence computed tomography. A particular type of x-ray source suitable for this is a line emitting liquid-jet-anode x-ray source. X-ray fluorescence is obtained using nanoparticles, preferably coated nanoparticles with a metallic core. The x-ray radiation from the x-ray source is shaped and filtered using energy dispersive optics before being delivered to the nanoparticles.

13 Claims, 4 Drawing Sheets

(51) Int. Cl.
   *G01N 23/223*    (2006.01)
   *H05G 2/00*      (2006.01)
   *A61K 49/00*     (2006.01)
   *A61K 49/04*     (2006.01)

(52) U.S. Cl.
   CPC .......... *A61B 6/4035* (2013.01); *A61B 6/4071* (2013.01); *A61B 6/4241* (2013.01); *A61K 49/0065* (2013.01); *A61K 49/0423* (2013.01); *G01N 23/223* (2013.01); *H05G 2/003* (2013.01); *H01J 2235/082* (2013.01)

(56) References Cited

OTHER PUBLICATIONS

Written Opinion (PCT/ISA/237) dated Mar. 18, 2015, by the European Patent Office as the International Searching Authority for International Application No. PCT/ EP2015/050011.

F. Zamponi et al., "Femtosecond hard x-ray plasma sources with a kilohertz repetition rate", Applied Physics A, Materials Science & Processing, Mar. 12, 2009, pp. 51-58, vol. 96, No. 1.

M. Bertilson et al., "High-resolution computed tomography with a compact soft x-ray microscope", Optics Express, Jan. 1, 2000, pp. 185-197, vol. 17, No. 13.

B. Kaulich et al., "Transmission of emission x-ray microscopy: operation modes, contrast mechanisms and applications", Journal of Physics: Condensed Matter, Feb. 4, 2011, pp. 1-23, vol. 23, No. 8.

H. M. Hertz et al., "Laboratory x-ray fluorescence tomography for high-resolution nanoparticle bio-imaging", Optics Letters, Optical Society of America, May 1, 2014, pp. 2790-2793, vol. 39, No. 9.

A. Moiz et al., "Order of Magnitude Sensitivity Increase in X-ray Fluorescence Computed Tomography (XFCT) Imaging With an Optimized Spectro-Spatial Detector Configuration: Theory and Simulation", IEEE Transaction of Medical Imaging, May 1, 2014, pp. 1119-1128, vol. 33, No. 5.

A. Moiz et al., "X-Ray Luminescence and X-Ray Fluorescence Computed Tomography: New Molecular Imaging Modalities", IEEE Access, Sep. 4, 2014, pp. 1051-1061, vol. 2.

B. L. Jones et al., "Experimental demonstration of benchtop x-ray fluorescence computed tomography (XFCT) of gold nanoparticle-loaded objects using lead- and tin-filtered polychromatic cone-beams", Physics in Medicine and Biology, 2012, pp. N457-N467, vol. 57.

* cited by examiner

X-RAY MICRO IMAGING

TECHNICAL FIELD

The present invention relates generally to molecular bio-imaging, and more particularly to x-ray fluorescence computed tomography.

BACKGROUND

Bio-imaging technologies are essential for clinical as well as preclinical medical research and daily medical practice. For any imaging system, resolution and contrast are key performance factors. Resolution refers to the spatial detail that can be revealed, while contrast includes a wide range of parameters, from simple physical signal-to-noise ratio to functional and molecular selectivity and sensitivity.

Functional and molecular imaging is becoming increasingly important both for research and in the clinic. In this context, "functional" refers to detecting changes in metabolism and "molecular" refers to measurements of biological processes on the molecular or cellular level. It is generally desired to be able to perform such imaging in vivo.

Several techniques for imaging exist in the prior art, such as magnetic resonance imaging (MRI), positron emission tomography (PET) and single-photon emission computed tomography (SPECT), which provide different aspects of such imaging (from humans or human sized subjects to smaller subjects such as mice). However, the spatial resolution of these techniques is low, typically a few millimeters (PET and SPECT) or down to about one millimeter (MRI). Similar limitations apply for small-animal research tools such as luceferin-based bio-luminescence. Fundamental constraints in the techniques make it hard to envision large upcoming improvements.

Recently, x-ray imaging has received more attention for higher resolution imaging, primarily for providing morphological data, but also directed towards functional and molecular imaging.

One example of a system and method for x-ray fluorescence computed tomography imaging is disclosed in WO 2011/084625, in which there is described x-ray fluorescence computed tomography (XFCT) for molecular imaging of various cells loaded with metallic nanoparticles using polychromatic diagnostic energy x-rays. The XFCT is performed of a plurality of metallic nanoparticles within a cell. The nanoparticles are sized and configured to not only have an affinity for cell compounds, but also have a size small enough to be able to enter the cell or multicellular structures like tumors or tissue. A polychromatic x-ray source at diagnostic energy levels is energized to cause x-ray fluorescence of the nanoparticles.

However, this prior art XFCT system comes with some serious drawbacks related to noise and background radiation in the generated signal. Excitation of the nanoparticles themselves as well as Compton scattering produce a considerable background signal that must be filtered out or otherwise handled in order to be able to detect the desired fluorescence. Filters, spline-function data fitting, and piecewise cubic Hermitian polynomial interpolation is used in order to filter out the background and enable identification of the desired fluorescence. All in all, this limits the resolution and contrast of this prior-art system considerably.

Attempts have been made by Bernard L Jones et al. (Phys. Med. Biol. 57 (2012), N457-N467) to improve XFCT systems that use gold nanoparticles (GNPs) as fluorescence targets, wherein the polychromatic x-ray spectrum was filtered using lead (Pb) or preferably tin (Sn) filters to provide a filtered polychromatic excitation spectrum. Such filtering was said to facilitate detection of $K_\alpha$ fluorescence peaks from the GNPs by increasing the signal-to-background ratio. They noted that the ratio of gold fluorescence signal to delivered dose increased exponentially with tin filter thickness. However, the scan time to produce the same magnitude of gold fluorescence signal also increased with tin filter thickness at a much higher rate. It was thus concluded that it was imperative to use a higher power x-ray tube for the XFCT scanning in order to take advantage of an increased signal-to-dose ratio from the use of thicker filters.

SUMMARY

The present invention is based on an understanding of the fundamental shortcomings of the prior art, and provides solutions that facilitate high resolution XFCT.

While it is generally preferred to use a pencil beam of x-rays to generate the useful fluorescence, the prior-art approach of providing collimators in the form of apertures (typically in thick lead blocks) entails a radical decrease in x-ray flux. Therefore, embodiments of the present invention make use of x-ray optics in the form of multilayer mirrors, or possibly Fresnel zone plates, to shape the x-rays into a suitable pencil beam.

The use of filters, as proposed by Jones et al. (cf. above) is associated with some very challenging drawbacks. As already acknowledged, the scan time to produce a given magnitude of gold fluorescence signal increases extremely rapidly with filter thickness, making it imperative to combine this filter approach with very high power x-ray tubes in order to take advantage of the monochromatizing effect provided by the filters. Moreover, the filters are only able to reduce the low-energy part of the x-ray spectrum, while higher-energy photons are passed through the filter. Even if some improvement of the signal-to-background ratio is obtained, there are still a considerable x-ray flux at higher energies that will generate a Compton background to the $K_\alpha$ fluorescence of interest.

The present invention provides a radical improvement of resolution and contrast in the field of x-ray fluorescence imaging by using a line emitting, quasi-monochromatic x-ray source for x-ray fluorescence computed tomography (XFCT).

A particular type of x-ray source suitable for this is a line emitting liquid-jet-anode x-ray source. This kind of x-ray source typically generates also a broad spectrum Bremsstrahlung background, although at levels considerably lower compared to the characteristic line emission. Such Bremsstrahlung is effectively reduced in embodiments of this invention by the use of energy-selective optics.

X-ray fluorescence is obtained using nanoparticles, preferably coated nanoparticles with a metallic core. The nanoparticles are present in a sample/subject to be imaged, and can be provided to the sample/subject in a number of ways which are per se known in the art.

By combining a line emitting, high-brightness liquid-jet-anode x-ray source, energy-selective beam forming x-ray optics, photon-counting and energy-dispersive detection and matched nanoparticle core materials, background radiation can be reduced and the signal-to-noise ratio increased drastically compared to other absorption- and fluorescence-based methods for detecting nanoparticles. This can lead to a tenfold improvement of observable spatial resolution and higher sensitivity, still at reasonable dose and exposure times.

The energy-selective beam forming x-ray optics will typically be adapted to provide band-pass filtering of the x-ray spectrum, thus reducing a considerable portion of the photons not useful for inducing fluorescence in the target nanoparticles. Thereby, a drastic reduction of the Compton background is obtained, thus leading to a higher signal-to-background ratio which in turn leads to shorter scan times particularly when used in conjunction with an energy dispersive, photon counting detector.

In order to take full advantage of the energy-selective beam forming x-ray optics, the x-ray source should have a high brightness. Sufficiently high brightness is typically not provided by regular x-ray tubes. Therefore, the present invention makes use of a line emitting liquid-jet-anode x-ray source that provides excellent luminosity and brightness, which enables shorter exposure times by virtue of a higher photon flux.

The term "quasi-monochromatic" is used herein to define radiation having a single or a few pronounced line emission energy peaks.

The term "nanoparticles" is used herein in the normal meaning thereof, i.e. particles that have an average diameter between 1 and 1000 nm, and typically not more than 100 nm.

In one aspect, the present invention relates to the use of a line emitting liquid-jet-anode x-ray source for XFCT.

In another aspect, the present invention relates to a method of performing XFCT.

In another aspect, the present invention relates to apparatus for XFCT.

In yet another aspect, the present invention relates to an XFCT image having sub-millimeter resolution.

BRIEF DESCRIPTION OF THE DRAWINGS

In the detailed description below, reference will be made to the accompanying drawings, in which:

FIG. 4a shows a tomographic reconstruction of a phantom; and

FIG. 4b shows a simulated image corresponding to the tomographic reconstruction of FIG. 4a;

DETAILED DESCRIPTION OF PREFERRED EMBODIMENTS

Figure 1:
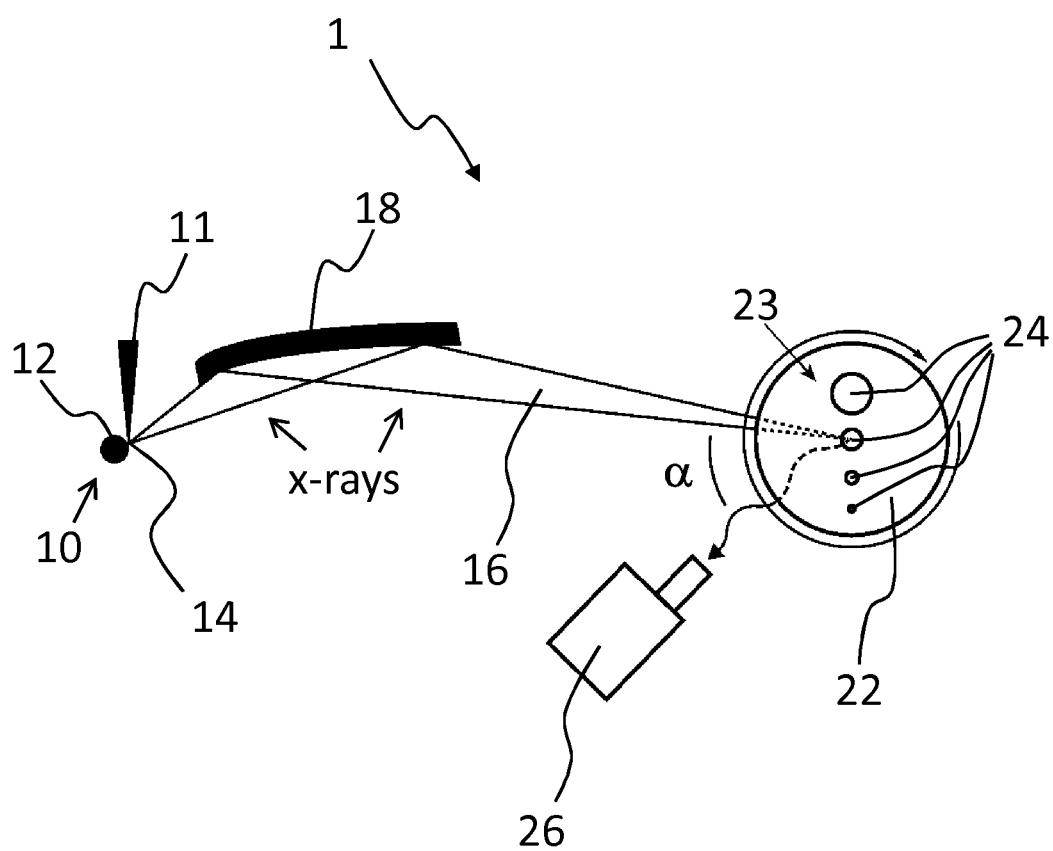
FIG. 1 schematically shows an experimental setup for an embodiment according to the present invention.

Preferred embodiments of the invention are based on line emitting, liquid-jet-anode x-ray sources of the kind disclosed in EP1305984 (Jettec AB). This x-ray source generates Bremsstrahlung and characteristic line emission in the hard x-ray region by forming a target jet propagating through an area of interaction, and by directing an electron beam onto the jet in the area of interaction. Hard x-ray radiation is thus formed essentially without heating the target jet to a plasma-forming temperature. Typically, the propagation speed of the target jet through the area of interaction is comparatively high, such as about 100 m/s. By using a liquid-jet-anode, the anode can support significantly higher electron power densities than a solid anode, and thus produce an x-ray output of extremely high brightness.

An electron-impact liquid-jet-anode x-ray source provides for excellent contrast, high spatial resolution and reasonable exposure times in general due to its quasi-monochromatic output above the Bremsstrahlung background. Moreover, due to the quickly regenerating nature of the liquid-jet-anode, very high electron-beam power density can be imposed, resulting in significantly higher brightness compared to other kinds of electron-impact x-ray sources, which enables a considerable improvement in count rates for x-ray fluorescence and thereby reduced exposure times.

An x-ray source of this kind is commercially available from Excillum AB, Kista (Sweden), currently marketed as MetalJet D1/D2™.

X-ray radiation can be obtained at different energies by proper selection of material for the liquid-jet-anode. A liquid jet of indium (In) provides line emission at around 25 keV (24.1 keV), bismuth (Bi) provides line emission at around 77 keV, and lead (Pb) provides line emission at around 75 keV. Also tin (Sn) can provide line emission at suitable energies.

The x-ray emission from the source is preferably shaped into a pencil beam using energy-selective x-ray optics, whereupon the pencil beam is incident upon a target comprising nanoparticles to induce x-ray fluorescence therefrom. The fluorescence is then detected using energy dispersive single-photon detection.

As will be described in more detail below, the monochromatizing effect of the energy-selective optics is used in an advantageous manner in order to reduce the Compton background of the x-ray fluorescence, and thereby improve signal-to-noise ratios in XFCT applications. The energy-selective optics is implemented to provide a bandpass filter that reduces both low-energy and high-energy photons emerging from the liquid-jet-anode x-ray source, while passing photons from the line emission of interest and forming these into a pencil beam for use in the XFCT to induce fluorescence in the nanoparticles. This bandpass filtering of the incoming x-ray spectrum thereby reduces the Compton background by filtering out both low-energy photons and high-energy photons which do not significantly add to the useful fluorescence but add to the Compton background. Thereby, the signal-to-background ratio is drastically increased in a very effective manner particularly when an energy dispersive, photon counting detector is used.

In an embodiment of the invention, the strong line emission of Indium at 24.1 keV from a liquid-metal-jet source is exploited to induce fluorescence in nanoparticles, which entails benefits of reduced exposure times and reduced background. The energy of 24.1 keV is suitable for rodent imaging, having a typical transmission of about 50% in 20-mm-sized soft-tissue objects.

The nanoparticles in this embodiment include Molybdenum (Mo), having an absorption band which is matched by the 24.1 keV x-ray emission. Mo has previously not been used for nanoparticle bio-imaging, but holds promise to be a suitable and acceptable material. The material has a limited toxicity due to its endogenous character, and it can also be suitably coated for improved biocompatibility.

FIG. 1 illustrates an experimental arrangement of an apparatus 1 for XFCT according to the invention. A liquid-metal-jet (liquid-jet-anode) x-ray source, schematically indicated at reference numeral 10, provided high brightness x-ray radiation at 24.1 keV line emission from a small spot

14. The x-ray emission from the source was shaped into a pencil beam 16 using elliptical x-ray optics 18 of montel type. The elliptical x-ray optics had a collection angle of 19.2 mrad and provided a 2.7 mrad pencil beam 16, theoretically enlarging the 20 µm diameter source spot 14 to about 80 µm. Imperfections in the optics 18, however, added further to the beam spot size, and the actual focal spot at the sample in this set-up was measured to be 125×145 µm². The line emission flux in the pencil beam at 24.1 keV was measured to be 1.1×10⁶ ph/s.

The x-ray source 10 of this embodiment was an electron-impact liquid-jet-anode apparatus (Excillum MetalJet D2™) operating at a power of 30 W in the e-beam 11 focused to an 8 µm spot on the liquid-jet-anode 12 to form the x-ray source spot 14. The liquid-jet-anode was composed of GaInSn and the effective line emission at 24.1 keV is obtained from the $K_\alpha$ line of the In component. Ga and Sn were added to the liquid-metal to obtain, for example, desired melting point and rheology characteristics.

In this embodiment, nanoparticles of molybdenum (Mo) were used, which have an absorption edge at 19.9 keV thus providing large absorption at the 24.1 keV line and $K_\alpha$ fluorescence at 17.4 keV. For Mo (Z=42) the fluorescence efficiency is 78% and the photo-electric absorption is 83%. The phantoms 23 used in this embodiment were 20 mm diameter PET plastic cylinders 22 with four holes 24 of different diameters (0.15; 0.3; 0.5; and 1.0 mm). PET was chosen because the x-ray optical properties thereof closely resembles those of soft tissue, and the diameter of the cylinders was chosen to match a typical mouse size.

The nanoparticles used in this embodiment were obtained from US Research Nanomaterials Inc. and electron microscopy showed that the size range thereof was rather broad, making them unsuitable for small-animal experiments but just fine for the proof-of-principle phantom experiment of this embodiment. The nanoparticles were dissolved in glycerol to different concentrations in the range 0.1-1.0 wt % and injected into the holes 24 of the PET cylinder. The use of glycerol prevented sedimentation within the experimental time frames.

Detection of the fluorescence was provided by means of a 5×5 mm CdTe detector 26 (Amptek XR-100T) that provided single-photon-counting energy-dispersive detection. The measured bandwidth of the detector at the 17.4 keV Mo $K_\alpha$ fluorescence was 0.6 keV FWHM. The detector was positioned at an angle α with respect to the x-ray pencil beam of about 25 degrees, as indicated in FIG. 1, in order to decrease detection of Compton scattering. Full tomographic data sets were recorded by translating and rotating the phantom, providing path-integrated fluorescence measurements for each line. With 200 integrated line measurements per projection (100 µm steps) and 100 projections over 360 degrees, the total required data acquisition time was in the range of 0.5-5 h depending on Mo concentration and signal-to-noise ratio.

Figure 2:
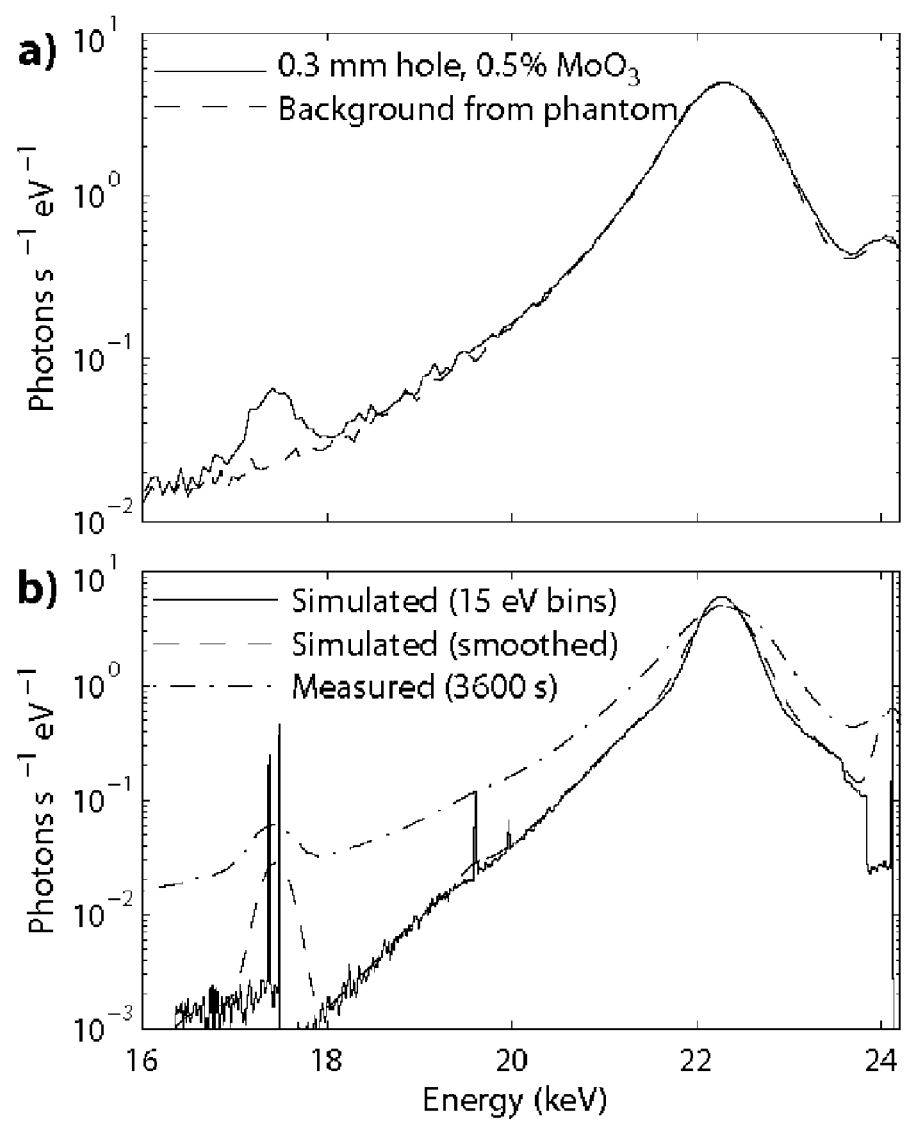
FIG. 2a shows a recorded spectrum of x-ray fluorescence from a phantom subject.
FIG. 2b shows a Monte Carlo simulation corresponding to the recorded spectrum of FIG. 2a, together with the experimental spectrum for comparison.

FIG. 2a shows the recorded spectrum when the x-ray pencil beam was scanned over the full 20 mm diameter of the phantom and the 0.3 mm diameter hole filled with 0.5 wt % Mo (solid line). The 17.4 keV Mo $K_\alpha$ fluorescence peak is clearly visible with a count rate of about 30 ph/s within the 0.6 keV bandwidth of the detector. The peak is well separated from the Compton scattered photons, which peak at 22.5 keV. The Mo $K_\alpha$ line at 19.6 keV is not visible at these low Mo concentration levels. For comparison, the spectrum from a second x-ray pencil beam, traversing no Mo inclusions, is also given in FIG. 2a (dashed line). Typically, a background of less than 10 ph/s was measured within the bandwidth detection window of the Mo $K_\alpha$ line. The exposure time for both recordings of FIG. 2a was 100 s.

FIG. 2b shows a corresponding Monte Carlo simulation of the spectrum with the 0.3 mm, 0.5 wt % Mo inclusion, both without smoothing for the bandwidth of the detector (solid line) and with such smoothing (dashed line). The high-resolution spectrum resolves the 17.37 keV and the 17.49 keV $K_\alpha$ double line. It is clear from the theoretical calculations that the major source of noise is the low-energy tail of the Compton scattering from the phantom. Compton scattering from the Mo itself is negligible at these small-sized and low-concentration inclusions. From FIG. 2b it is also evident that the signal-to-noise ratio can be increased significantly by using a detector of smaller bandwidth. FIG. 2b also shows the experimental spectrum for comparison (dash-dotted line). The data sets agree well, although the experimental background is higher than the theoretical, possibly due to electronic detector noise.

Figure 3A:
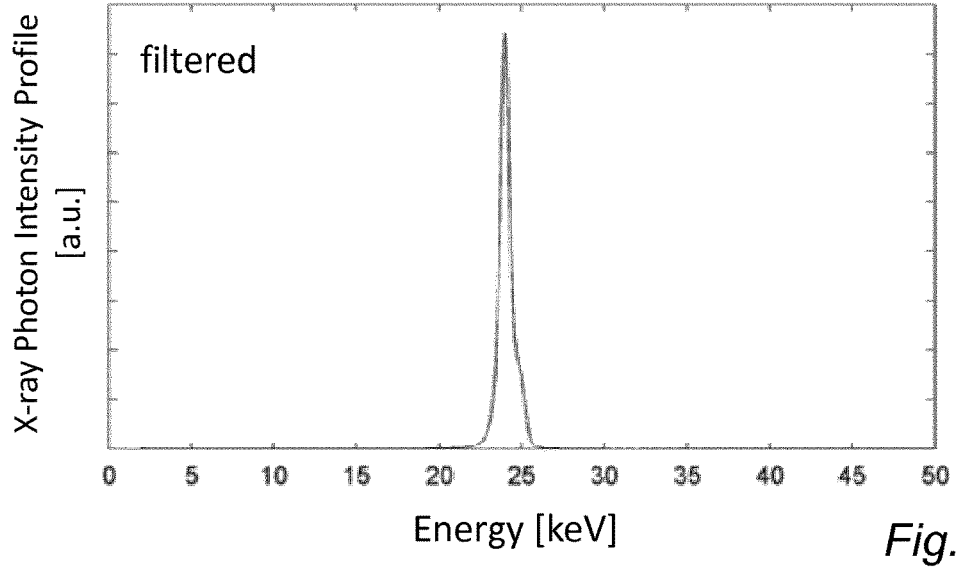
FIG. 3a shows a spectrum of x-ray radiation from the line emitting liquid-jet-anode x-ray source after having passed an energy selective mirror arrangement.
Figure 3B:
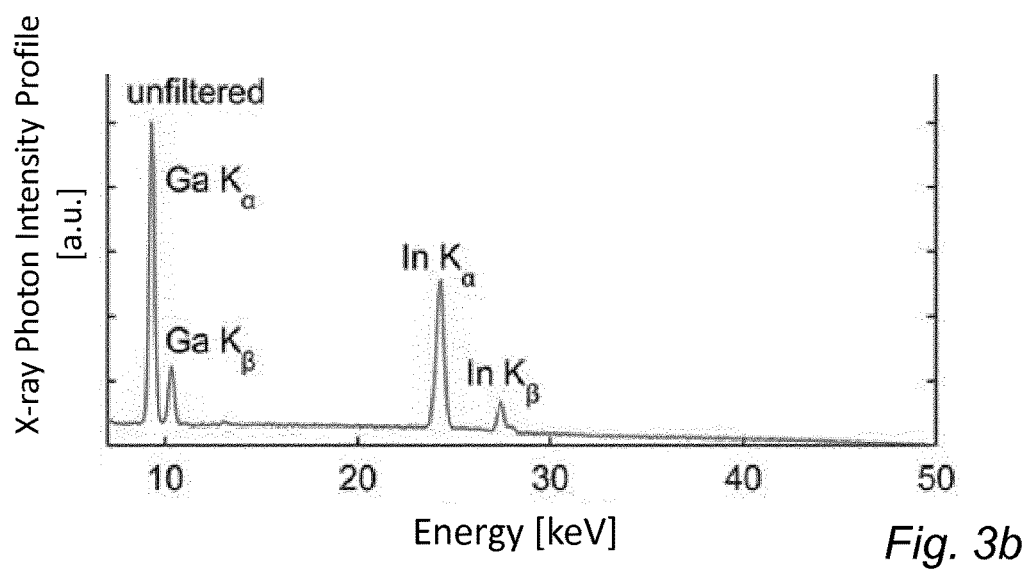
FIG. 3b shows a corresponding spectrum of the incoming x-ray radiation before monochromatization by the energy selective mirror arrangement.

In embodiments of the present invention, multilayer mirrors are utilized in order to form the x-ray output from the line emitting liquid-jet-anode into a pencil beam useful for XFCT and at the same time provide a monochromatizing effect on the incoming x-ray radiation. FIGS. 3a and 3b show a measured spectrum of the pencil beam after having been monochromatized and formed by a multilayer mirror arrangement, and of the incoming x-ray radiation before the mirror arrangement, respectively. It should be noted that the spectrum graphs of FIGS. 3a and 3b were constructed using different scales for the vertical axis, but the monochromatizing effect of the mirror arrangement is apparent and only the In $K_\alpha$ line appears in the spectrum of the filtered radiation. The mirror arrangement has a strong monochromatizing effect on the spectrum, producing a comparatively narrow-band spectrum having a width of about 1 keV FWHM. Such narrow-band excitation spectrum for the XFCT allows for a considerable reduction of Compton background compared to prior art technology, and avoids at the same time the drastic reduction in photon count that is caused by prior art filter techniques (cf. Jones et al. above).

One suitable configuration is a so-called montel mirror, in which at least two elliptical mirrors are placed perpendicular to each other and side-by-side to form the pencil beam. Montel optics per se is known in the prior art.

Figure 4:
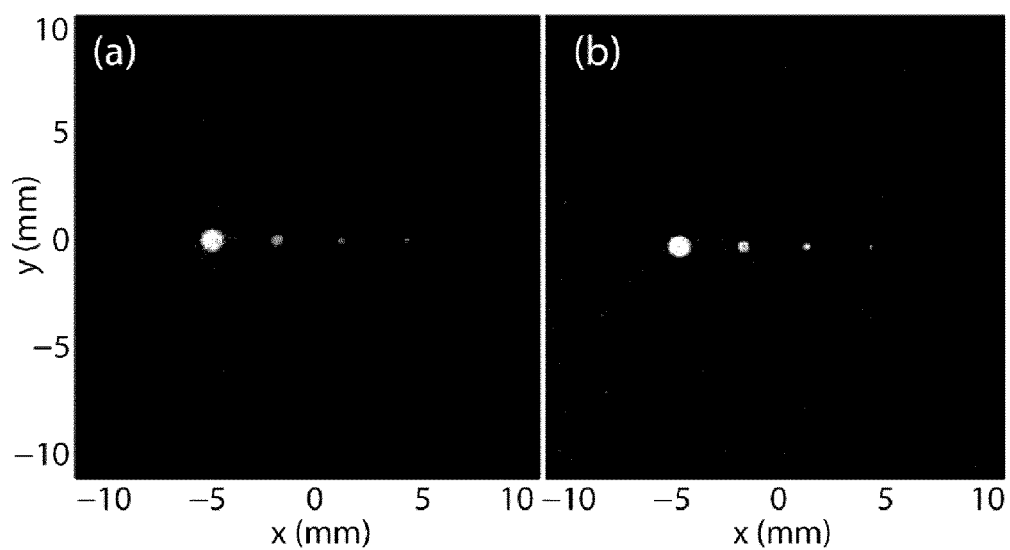

FIG. 4a shows the tomographic reconstruction of a phantom having 0.5 wt % Mo in all four holes. The tomographic reconstruction was performed with a filtered back-projection algorithm on the 100 projections. Each projection contained 200 data points, where each point was calculated from the spectrally integrated in-band photon numbers in the corresponding path-integrated fluorescence measurement and with the Compton-tail background subtracted. In this experiment, the measurement time was 1 s per integrated projection measurement. This is 50× faster than previous work presented by Jones et al. in Phys Med Biol 57, N457 (2012). The tomographic reconstruction of FIG. 4a clearly demonstrates that 150 µm objects can be imaged at reasonable exposure times. The dose delivered was 700 mGy, which is on the high side for small-animal experiments but it can easily be reduced as will be discussed below.

FIG. 4b shows a simulation of the same experiment. The correlation between experiment and simulation is excellent. From measurements of the observability, it is concluded that the 1 mm and 0.15 mm diameter inclusions have an $SNR^2$ of 7000 and 80, respectively. Considering that an $SNR^2$ of 25 is generally considered sufficient to allow observations of a feature, there is a good margin for dose and exposure time reduction already in this proof-of-concept arrangement.

Embodiments of the present invention provide the possibility of performing tomographic x-ray fluorescence nanoparticle imaging with significantly improved resolution and reduced exposure times, and at a dose range relevant for small animal imaging. In addition, the concept is scalable and several improvements can be implemented according to the invention, such as increasing the In $K_\alpha$ flux by using a more powerful line emitting liquid-jet-anode x-ray source, improving the mirror performance to reduce the x-ray spot size, and increasing the detector area. With a 10× increase of the In $K_\alpha$ flux, a 10× larger detector area, and an improved mirror, simulations show that sub-100 μm resolution tomographic imaging of <0.1 wt % concentration of Mo with an $SNR^2$ of 25 can be performed with about 2 ms exposure time per integrated measurement. For a 20 mm object, 100 μm step size and 180 projections, this results in total exposure times of 10-30 s. The total dose of such a tomographic recording is estimated to be <100 mGy, well within the acceptable range for small-animal research. Thus, the present invention provides a path to small-animal molecular imaging with higher resolution than any existing method, already with the present state of technology. Improvements on the detector side (area and bandwidth) will further reduce exposure times and dose.

Another aspect of the present invention relates to an XFCT image having sub-millimeter resolution. The inventive XFCT image is obtainable by generating x-ray radiation using a line emitting liquid-jet-anode x-ray source; shaping the x-ray radiation into a pencil beam using energy-selective optics; delivering the pencil beam to nanoparticles present in a sample to induce x-ray fluorescence therefrom; detecting the fluorescence from the nanoparticles using energy dispersive single-photon detection; and finally forming the XFCT image from the detected fluorescence.

It is envisaged that embodiments of the present invention will be used for in vivo experiments. This would require that nanoparticles are present in the target somehow. Targeting of nanoparticles to a specific location can be active or passive. Passive targeting may for example exploit the enhanced permeability and retention (EPR) due to leakiness of tumor vasculature, while active targeting could employ affinity ligands on the nanoparticles that bind to tumor-specific biomarkers or specific receptors. Targeting of nanoparticles per se is known generally within the field of nanomedicine, where the scope is wider than imaging (e.g. targeted drug delivery and therapy) and metallic nanoparticles (liposomes, carbon, silica, etc.).

In embodiments of the present invention, it is particularly preferred to use nanoparticles of molybdenum (Mo) or tungsten (W), or alternatively of gold (Au) or other high-Z materials. Molybdenum has an x-ray absorption band that overlaps an x-ray output at 24.1 keV from the In $K_\alpha$ line of the liquid-jet-anode x-ray source, and also appears to have a low toxicity. Tungsten has an x-ray absorption band at higher energies that overlaps with higher energy x-ray radiation that may prove useful for imaging of larger subject, even up to human-sized subjects. Due to its known toxicity, however, tungsten nanoparticles are preferably appropriately coated in order enhance biocompatibility and facilitate in vivo use thereof.

A particularly preferred combination is to use indium in the liquid-jet-anode x-ray source to produce $K_\alpha$ emission at about 24.1 keV and nanoparticles comprising molybdenum, as detailed above. Molybdenum has an absorption edge at 19.9 keV thus providing large absorption at the 24.1 keV line and produces $K_\alpha$ fluorescence at 17.4 keV. For molybdenum (Z=42) the fluorescence efficiency is 78% and the photoelectric absorption is 83%. The energy of 24.1 keV is suitable for small-animal (rodent) imaging, having a typical transmission of about 50% in 20-mm-sized soft-tissue objects.

It will be understood that the technology disclosed herein can involve multiple x-ray beams for causing fluorescence in the nanoparticles. Such multiple beams may be generally parallel to each other, or may be devised to enter the sample from different directions. The use of multiple beams can be readily implemented by the skilled person after having read and understood the present disclosure.

It should also be noted that the present invention can be implemented together with traditional absorption techniques. Parallel measurements of the absorption of the incoming x-ray beam can be used for improving the accuracy of the reconstruction by overlaying the absorption tomographic map with the fluorescence tomographic map. This extra information comes at no dose expense and may become particularly advantageous when bone absorption needs to be compensated for.

After having read the description above and the appended claims, a person of ordinary skill in the art will be able to deduce various embodiments according to the present invention.

In conclusion, the present invention provides improvements of resolution and contrast in the field of x-ray imaging by using a line emitting, quasi-monochromatic x-ray source for x-ray fluorescence computed tomography. A particular type of x-ray source suitable for this is a line emitting liquid-jet-anode x-ray source. X-ray fluorescence is obtained using nanoparticles, preferably coated nanoparticles with a metallic core. The x-ray radiation from the x-ray source is shaped and filtered using energy dispersive optics before being delivered to the nanoparticles.

The invention claimed is:

1. A method of performing x-ray fluorescence computed tomography, comprising the steps of:
   generating x-ray radiation using a line emitting liquid-jet-anode x-ray source;
   shaping and bandpass filtering the x-ray radiation using energy-selective optics;
   delivering the x-ray radiation to nanoparticles present in a sample to induce x-ray fluorescence;
   detecting the fluorescence from the nanoparticles using energy dispersive detection; and
   forming an x-ray image from the detected fluorescence.

2. The method of claim 1, wherein the step of detecting the fluorescence is performed using energy dispersive single-photon detection.

3. The method of claim 1, further comprising translating and/or rotating the sample.

4. The method of claim 1, wherein the liquid-jet-anode of the x-ray source used in the generating step comprises indium, bismuth, lead, tin or a combination thereof, optionally with an addition of gallium and/or tin.

5. The method of claim 4, wherein the liquid-jet-anode of the x-ray source used in the generating step comprises indium, and wherein the nanoparticles used in the delivering step comprises molybdenum.

6. Apparatus for x-ray fluorescence computed tomography, comprising
   a line emitting liquid-jet-anode x-ray source;
   energy-selective beam shaping optics effective to provide bandpass filtering of x-rays emitted from the line emitting liquid-jet-anode x-ray source, and to shape the emitted x-rays into a pencil beam useful for inducing fluorescence in nanoparticles; and an energy dispersive single-photon detector for detecting fluorescence induced by the pencil beam in nanoparticles.

7. Apparatus according to claim 6, wherein said energy-selective beam shaping optics comprises a mirror arrangement of montel type.

8. Apparatus according to claim 6, wherein said energy-selective beam shaping optics comprises one or more zone plates.

9. A method comprising using a line emitting liquid-jet-anode x-ray source for x-ray fluorescence computed tomography, wherein
x-ray radiation emitted from the x-ray source is shaped and bandpass filtered using energy-selective optics into a pencil beam;
and the pencil beam of x-ray radiation is delivered to nanoparticles present in a sample.

10. The method according to claim 9, wherein
fluorescence from the nanoparticles is detected using energy dispersive detection; and an x-ray image is formed from the detected fluorescence.

11. The method according to claim 9, wherein the liquid-jet-anode of the x-ray source comprises indium, bismuth, lead, tin or a combination thereof, optionally with an addition of gallium and/or tin.

12. The method according to claim 9, wherein the nanoparticles comprise molybdenum, tungsten, gold or a combination thereof.

13. The method according to claim 9, wherein the liquid-jet-anode of the x-ray source comprises indium; and wherein the nanoparticles comprise molybdenum.

\* \* \* \* \*